US00PP20309P2

(12) United States Plant Patent
Ackerman et al.

(10) Patent No.: US PP20,309 P2
(45) Date of Patent: Sep. 15, 2009

(54) STRAWBERRY PLANT NAMED 'PREMIER'

(50) Latin Name: *Fragaria ananassa*
Varietal Denomination: PREMIER

(75) Inventors: Stephen M. Ackerman, Salinas, CA (US); Steven D. Nelson, Watsonville, CA (US); Michael D. Nelson, Watsonville, CA (US)

(73) Assignees: Plant Sciences, Inc., Watsonville, CA (US); Berry R&D, Inc., Watsonville, CA (US)

( * ) Notice: Subject to any disclaimer, the term of this patent is extended or adjusted under 35 U.S.C. 154(b) by 0 days.

(21) Appl. No.: 12/218,466

(22) Filed: Jul. 15, 2008

(51) Int. Cl.
*A01H 5/00* (2006.01)

(52) U.S. Cl. ..... Plt./209
(58) Field of Classification Search ..... Plt./208, Plt./209
See application file for complete search history.

*Primary Examiner*—Kent L Bell
(74) *Attorney, Agent, or Firm*—Foley & Lardner LLP

(57) ABSTRACT

This invention relates to a new and distinct variety of strawberry plant named 'PREMIER'. This new strawberry plant named 'PREMIER' is primarily adapted to the growing conditions of the central coast of California, and is primarily characterized by its medium red fruit color; large fruit size; conical to ovate fruit shape; large calyx; medium sized plant; medium to dark green foliage color; medium sized foliage; short fruiting trusses; and strong pubescence of the fruiting truss.

5 Drawing Sheets

Latin name of the genus and species of the plant claimed: *Fragaria ananassa.*
Variety denomination: 'PREMIER'.

BACKGROUND OF THE INVENTION

The present invention relates to a new and distinct strawberry variety named 'PREMIER'. This new variety is a result of a controlled cross made in 2001 between strawberry variety designated 'PS-1269' (patented, U.S. Plant Pat. No. 10,686) and strawberry variety designated 'PS-3003' (unpatented) in an ongoing breeding program. The variety is botanically known as *Fragaria ananassa.* The new variety is distinguished from its parents primarily in fruit color.

The seedling resulting from the aforementioned cross was selected from a controlled breeding plot in Ventura County, Calif. in the fall of 2003. After its selection, the new variety was asexually propagated by stolons in a nursery located in San Joaquin County, Calif. The new variety was extensively tested over the next several years in fruiting fields in Ventura County, Calif. This propagation has demonstrated that the combination of traits disclosed herein as characterizing the new variety are fixed and remain true to type through successive generations of asexual reproduction.

BRIEF SUMMARY OF THE INVENTION

'PREMIER' is primarily adapted to the climate and growing conditions of the central coast of California. This region provides the necessary winter temperatures required for it to produce a strong vigorous plant and to remain in fruit production from October through December. The nearby Pacific Ocean provides the needed humidity and moderate temperatures to maintain fruit quality during the fall production months.

The following traits have been repeatedly observed and are determined to be unique characteristics of 'PREMIER', which in combination distinguish this strawberry plant as a new and distinct variety:

1. Medium red fruit color;
2. Large fruit size;
3. Conical to ovate fruit shape;
4. Large calyx;
5. Medium sized plant;
6. Medium to dark green foliage color;
7. Medium sized foliage;
8. Short fruiting trusses; and
9. Strong pubescence of the fruiting truss.

The strawberry variety that is believed to be most closely related to the new strawberry variety 'PREMIER' is 'PS-2880' (patented, U.S. Plant Pat. No. 15,597). In comparison to the similar strawberry variety 'PS-2880', the new strawberry variety 'PREMIER' differs by the following combination of characteristics as described in Table 1:

TABLE 1

| Characteristic | 'PREMIER' | 'PS-2880' (U.S. Plant Pat. No. 15,597) |
|---|---|---|
| 1. Color of mature fruit | Medium red | Red |
| 2. Average fruit weight (gm) | 24.7 | 20.7 |
| 3. Predominant fruit shape | Conical to ovate | Conical to wedged |
| 4. Marketable yield (gm/plt) | 381 | 457 |
| 5. Unevenness of fruit surface | Absent or very weak | Medium to strong |
| 6. Insertion of achenes | Level with the surface | Above the surface |
| 7. Attitude of calyx | Spreading | Spreading to reflexed |
| 8. Plant size | Medium | Medium to large |

TABLE 1-continued

| Characteristic | 'PREMIER' | 'PS-2880' (U.S. Plant Pat. No. 15,597) |
|---|---|---|
| 9. Foliage color (upper surface) | Medium to dark green | Medium to light green |
| 10. Petiole pubescence | Sparce | Moderate |
| 11. Fruiting truss length (cm) | 20.3 | 27.1 |
| 12. Fruiting truss pubescence | Strong | Medium |

For identification a series of AFLP molecular markers have been determined for this new variety.

BRIEF DESCRIPTIONS OF THE PHOTOGRAPHS

The accompanying color photographs illustrate the overall appearance of typical specimens of the new strawberry variety 'PREMIER', at various stages of development as true as it is reasonably possible with color reproductions of this type. Color in the photographs may differ slightly from the color value cited in the botanical description which accurately describe the color of 'PREMIER'. The depicted plant and plant parts of the new strawberry variety 'PREMIER' were taken in Ventura County, Calif., and are approximately 3 to 4 months old:

DETAILED BOTANICAL DESCRIPTION

Figure 1:
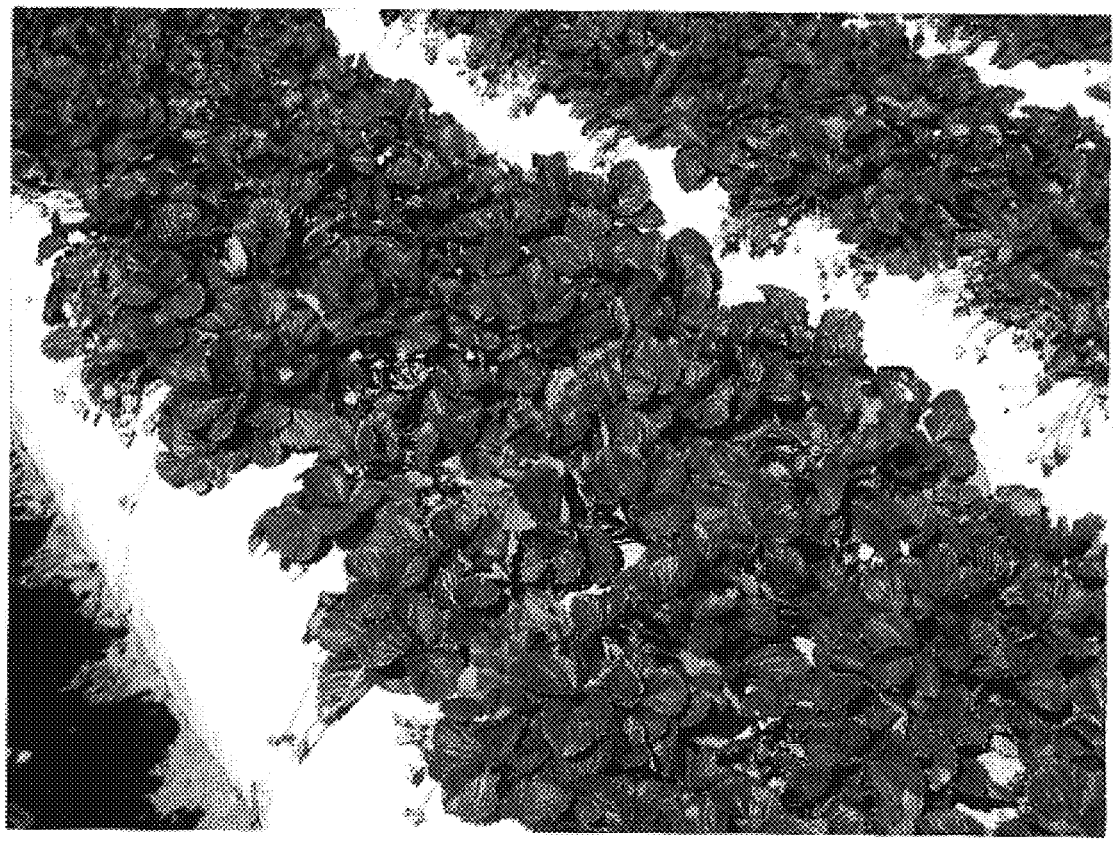
FIG. 1 shows typical fruiting field characteristics of 'PREMIER' taken in the month of October 2007.
Figure 2:
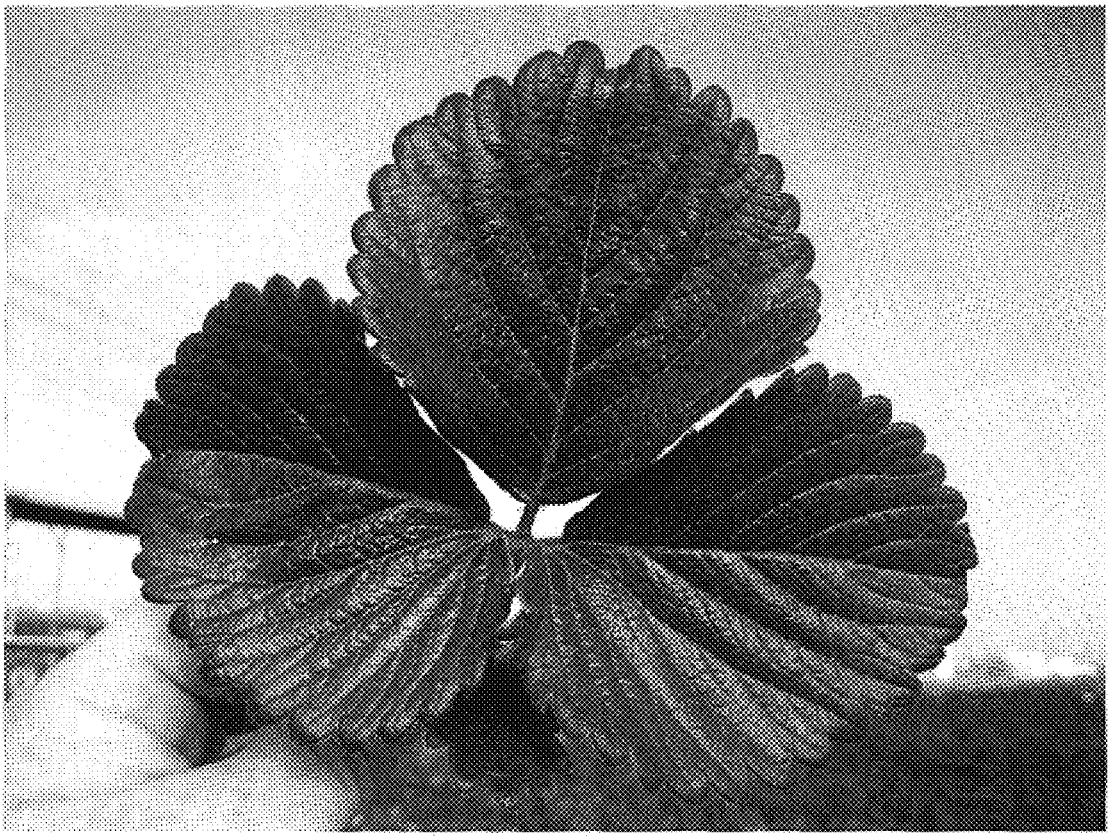
FIG. 2 shows a close-up view of typical leaf structure of 'PREMIER' taken in the month of November 2007.
Figure 3:
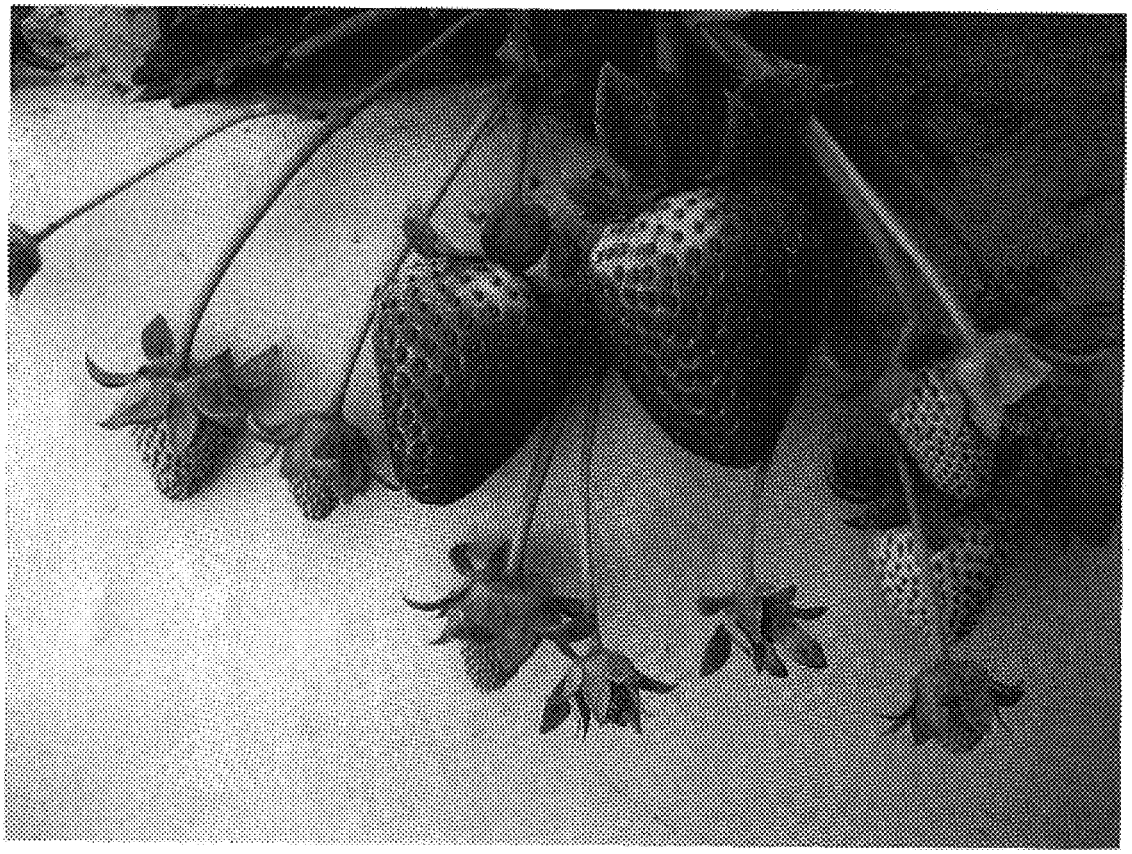
FIG. 3 shows typical mature and immature fruit of 'PREMIER' taken in the month of October 2007.
Figure 4:
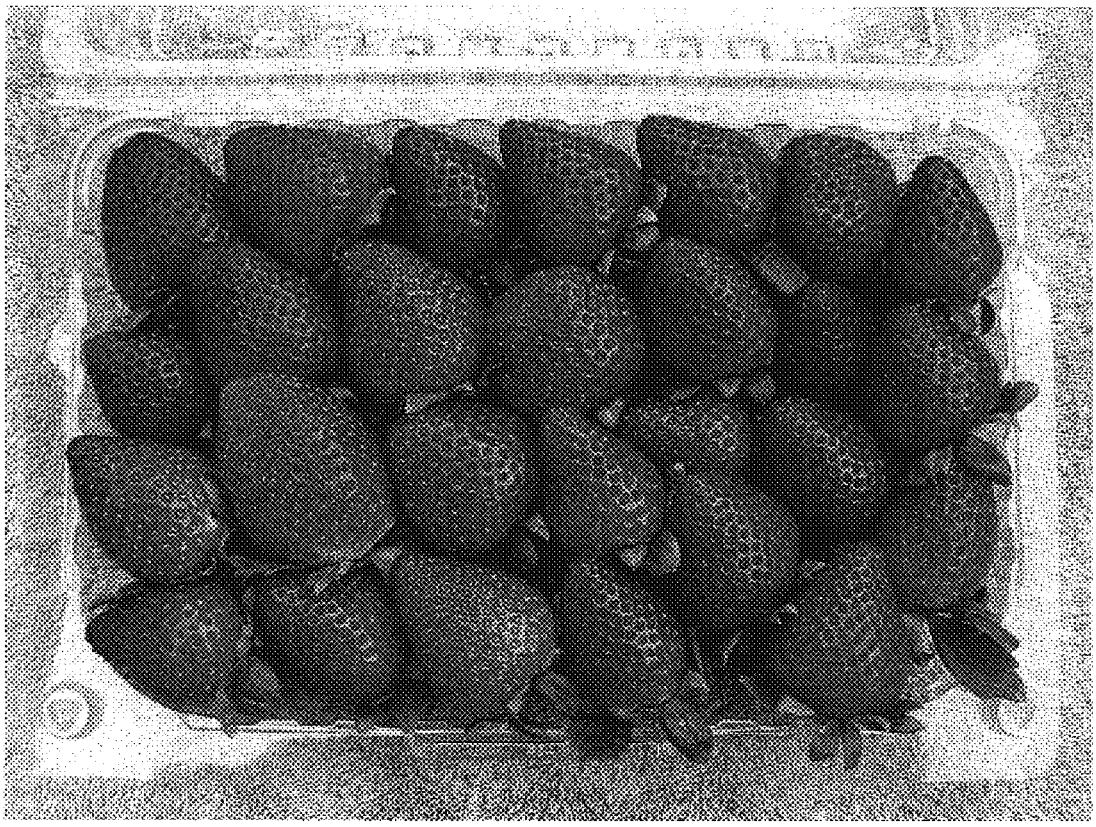
FIG. 4 shows a close-up view of mature fruit of 'PREMIER' taken in the month of October 2007.
Figure 5:
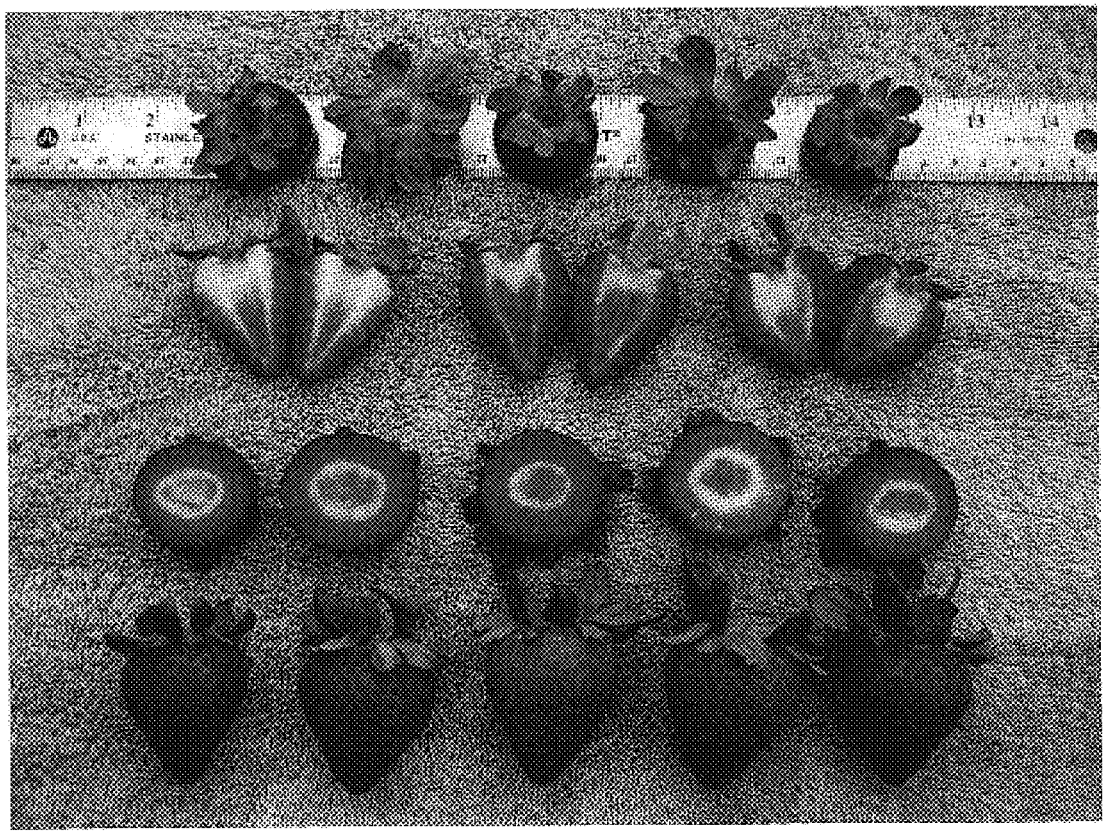
FIG. 5 shows typical internal and external mature fruit characteristics of 'PREMIER' taken in the month of October 2007.

'PREMIER' has not been observed under all possible environmental conditions. The characteristics of the new variety may vary in detail, depending upon variations in environmental factors, including weather (temperature, humidity and light intensity), day length, soil type and location.

The aforementioned photographs, together with the following description of the new variety 'PREMIER', unless otherwise noted, is based on observations taken during the 2007 growing season in Ventura County, Calif. These measurements and ratings were taken from plants of 'PREMIER' dug from a low-elevation nursery located in San Joaquin County, Calif. during late January 2007 and planted approximately 6 months later in Ventura County, Calif. The approximate age of the observed plants is 3 to 4 months. Yield observations and fruit quality characteristics are averaged from four years of data collected from the 2004 through 2007 growing seasons. Flower measurements and characteristics are from secondary flowers unless otherwise noted. Fruit characteristics and measurements are from secondary fruit unless otherwise noted.

Color terminology where noted follows the Munsell Book of Colors, Munsell Colors, Baltimore, Md. (1976).

The following tables 2–8 describe fruit, plant, stolon, foliage, fruiting truss, flower and pest disease characteristics of the new strawberry 'PREMIER' in comparison to the similar strawberry variety 'PS-2880' (patented, U.S. Plant Pat. No. 15,597).

TABLE 2

FRUIT CHARACTERISTICS

| Characteristic | 'PREMIER' | 'PS-2880' (U.S. Plant Pat. No. 15,597) |
|---|---|---|
| Color of mature fruit | 7.5R 3/8 to 4/10 Medium red | 7.5R 4/8 to 3/8 Red |
| Color of internal flesh | 7.5R 3/12 to 4/12 Medium red | 7.5R 3/12 to 4/12 Medium red |
| Length (cm) | 4.5 | 4.7 |
| Width (cm) | 3.8 | 3.6 |
| Ratio length/width | 1.20 Slightly longer than broad | 1.29 Slightly longer than broad |
| Calyx diameter (cm) | 6.0 | 5.4 |
| Average weight (gm) | 24.7 | 20.7 |
| Achene color | 5Y 6/8 to 7.5R 3/8 Ranges from medium yellow to medium red | 5Y 6/8 to 7.5R 3/8 Ranges from medium yellow to medium red |
| Achene weight (mg) | 0.50 | 0.53 |
| Achenes per berry | 358 | 364 |
| Marketable yield (gm/plt) | 381 | 457 |
| Fruit size | Large | Medium |
| Predominant shape | Ranges from conical to ovate | Ranges from conical to wedged |
| Difference in shapes between primary and secondary fruit | None or very slight | Moderate |
| Band without achenes | Absent or very narrow | Absent or very narrow |
| Unevenness of surface | Absent or very weak | Medium to strong |
| Evenness of color | Ranges from slightly uneven to even | Ranges from even to slightly uneven |
| Glossiness | Ranges from medium to strong | Ranges from medium to strong |
| Insertion of achenes | Level with the surface | Above the surface |
| Insertion of calyx | In the basin | Ranges from in the basin to level with the fruit |
| Attitude of the calyx | Spreading | Ranges from spreading to reflexed |
| Size of calyx in relation to fruit diameter | Much larger | Slightly larger |
| Adherence of calyx | Strong | Weak |
| Firmness of skin | Medium | Medium |
| Firmness of flesh | Medium | Firm |
| Distribution of red color of the flesh | Marginal and central | Marginal and central |
| Hollow center expression | Weak | Ranges from strong to moderate |
| Flavor | Fair | Fair to good |
| Soluble solids (% brix) | 7.4 | 7.7 |
| Time of first flowering | Medium | Ranges from early to medium |
| Time of first harvesting | Medium | Ranges from early to medium |
| Harvest period | Late September to mid December | Late September to mid December |
| Type of bearing | Fully everbearing | Fully everbearing |

TABLE 3

PLANT CHARACTERISTICS

| Characteristic | 'PREMIER' | 'PS-2880' (U.S. Plant Pat. No. 15,597) |
|---|---|---|
| Height (cm) | 20.6 | 26.4 |
| Spread (cm) | 35.3 | 35.8 |
| Size | Medium | Ranges from medium to large |
| Habit | Globose | Globose |

TABLE 3-continued

| PLANT CHARACTERISTICS | | |
|---|---|---|
| Characteristic | 'PREMIER' | 'PS-2880' (U.S. Plant Pat. No. 15,597) |
| Density | Medium | Medium |
| Vigor | Medium | Ranges from medium to strong |

TABLE 4

| STOLON CHARACTERISTICS | | |
|---|---|---|
| Characteristic | 'PREMIER' | 'PS-2880' (U.S. Plant Pat. No. 15,597) |
| Average number per plant | 10.0 | 5.3 |
| Anthocyanin intensity | Ranges from weak to medium | Medium |
| Anthocyanin coloration | 7.5R 4/8 to 5/8 | 7.5R 4/6 to 5/6 |
| Diameter at bract (mm) | 3.8 | 3.3 |
| | Thick | Ranges from medium to thick |
| Pubescence | Medium | Strong |

TABLE 5

| FOLIAGE CHARACTERISTICS | | |
|---|---|---|
| Characteristic | 'PREMIER' | 'PS-2880' (U.S. Plant Pat. No. 15,597) |
| Foliage: | | |
| Color of upper surface | 7.5GY 2/4 to 3/4 | 7.5GY 3/4 to 4/4 |
| | Ranges from medium to dark green | Ranges from light to medium green |
| Color of under side | 5GY 5/4 to 6/4 | 5GY 5/4 to 6/4 |
| | Light grey green | Light grey green |
| Shape in cross section | Slightly concave | Ranges from slightly concave to flat |
| Interveinal blistering | Medium | Ranges from medium to strong |
| Glossiness | Ranges from medium to strong | Ranges from medium to strong |
| Number of leaflets | Three | Three |
| Terminal Leaflet: | | |
| Length (cm) | 8.3 | 10.3 |
| Width (cm) | 8.1 | 8.8 |
| Length/width ratio | 1.02 | 1.18 |
| Serrations/leaf | 22.8 | 22.9 |
| Size | Medium | Ranges from medium to large |
| Shape of base | Obtuse | Acute |
| Shape of teeth | Obtuse | Obtuse |
| Petiole: | | |
| Petiole color | 2.5GY 5/6 to 5/8 | 5GY 6/6 to 7/6 |
| | Medium yellow green | Medium yellow green |
| Length (cm) | 12.0 | 13.9 |
| Diameter (mm) | 4.2 | 4.3 |
| Petiolule color | 2.5GY 5/6 to 5/8 | 5GY 6/6 to 7/6 |
| | Medium yellow green | Medium yellow green |
| Petiolule length (mm) | 10.3 | 15.3 |
| Pubescence | Sparce | Moderate |
| Attitude of hairs | Slightly outward | Slightly outward |

TABLE 5-continued

| FOLIAGE CHARACTERISTICS | | |
|---|---|---|
| Characteristic | 'PREMIER' | 'PS-2880' (U.S. Plant Pat. No. 15,597) |
| Stipule: | | |
| Color | 2.5GY 5/6 to 6/6 | 2.5GY 5/6 to 6/6 |
| | Medium yellow green | Medium yellow green |
| Length (mm) | 26.1 | 26.3 |
| Width (mm) | 12.3 | 9.2 |
| Anthocyanin intensity | Medium | Absent or very weak |
| Anthocyanin color | 10RP 4/8 to 4/10 | 10RP 5/6 to 5/8 |
| | Red purple | Red purple |
| Length (cm) | 20.3 | 27.1 |
| Flower position relative to foliage | Ranges from level with to beneath the foliage | Level with the foliage |
| Anthocyanin intensity | Medium | Weak |
| Anthocyanin color | 10RP 4/8 to 5/8 | 10RP 5/6 to 6/6 |
| | Red purple | Red purple |
| Pubescence | Strong | Medium |
| Attitude at first pick | Prostrate | Prostrate |

TABLE 6

| FRUITING TRUSS CHARACTERISTICS | | |
|---|---|---|
| Characteristic | 'PREMIER' | 'PS-2880' (U.S. Plant Pat. No. 15,597) |
| Length (cm) | 20.3 | 27.1 |
| Flower position relative to foliage | Ranges from level with to beneath the foliage | Level with the foliage |
| Anthocyanin instensity | Medium | Weak |
| Anthocyanin color | 10RP 4/8 to 5/8 | 10RP 5/6 to 6/6 |
| | Red purple | Red purple |
| Pubescence | Strong | Medium |
| Attitude at first pick | Prostrate | Prostrate |

TABLE 7

| FLOWER CHARACTERISTICS | | |
|---|---|---|
| Characteristic | 'PREMIER' | 'PS-2880' (U.S. Plant Pat. No. 15,597) |
| Petal color | N 9.5/90.0% R to 9.25/84.2% R | N 9.5/90.0% R to 9.25/84.2% R |
| | White | White |
| Corolla diameter (mm) | 32.7 | 33.6 |
| Calyx diameter (mm) | 39.5 | 34.1 |
| Petal length (mm) | 12.8 | 13.0 |
| Petal width (mm) | 12.7 | 13.8 |
| Petal length/width ratio | 1.01 | 0.95 |
| Petals/flower | 5.4 | 6.5 |
| Sepal color | 5GY 3/6 to 4/6 | 5GY 4/4 to 4/6 |
| | Medium yellow green | Medium yellow green |
| Sepal length (mm) | 15.6 | 12.3 |

TABLE 7-continued

| FLOWER CHARACTERISTICS | | |
|---|---|---|
| Characteristic | 'PREMIER' | 'PS-2880' (U.S. Plant Pat. No. 15,597) |
| Sepal width (mm) | 7.1 | 4.4 |
| Sepal length/width ratio | 2.21 | 2.78 |
| Sepals/flower | 10.8 | 12.3 |
| Size of calyx relative to corolla | Larger | Ranges from same size to larger |
| Size of inner calyx relative to outer calyx | Smaller | Smaller |
| Relative position of petals | Overlapping | Overlapping |

TABLE 8

| PEST AND DISEASE REACTIONS | | |
|---|---|---|
| Characteristic | 'PREMIER' | 'PS-2880' (U.S. Plant Pat. No. 15,597) |
| Two spotted spider mite | Moderately susceptible | Moderately susceptible |
| Lygus bug | Susceptible | Susceptible |
| Flower thrips | Moderately susceptible | Moderately susceptible |
| Powdery mildew | Susceptible | Susceptible |
| Botrytis fruit rot | Moderately susceptible | Moderately susceptible |
| Angular leaf spot | Moderately susceptible | Susceptible |

We claim:

1. A new and distinct strawberry plant named 'PREMIER', as herein described and illustrated by the characteristics set forth above.

* * * * *